US012590964B2

(12) United States Patent
Daunert et al.

(10) Patent No.: US 12,590,964 B2
(45) Date of Patent: Mar. 31, 2026

(54) MATERIALS AND METHODS FOR EXTRACELLULAR VESICLE DETECTION

(71) Applicant: UNIVERSITY OF MIAMI, Miami, FL (US)

(72) Inventors: Sylvia Daunert, Miami, FL (US); Yu-Ping Yang, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 893 days.

(21) Appl. No.: 17/784,170

(22) PCT Filed: Dec. 11, 2020

(86) PCT No.: PCT/US2020/064576
§ 371 (c)(1),
(2) Date: Jun. 10, 2022

(87) PCT Pub. No.: WO2021/119470
PCT Pub. Date: Jun. 17, 2021

(65) Prior Publication Data
US 2023/0051398 A1     Feb. 16, 2023

Related U.S. Application Data

(60) Provisional application No. 62/947,149, filed on Dec. 12, 2019.

(51) Int. Cl.
| | |
|---|---|
| *G01N 33/57545* | (2026.01) |
| *G01N 21/76* | (2006.01) |
| *G01N 33/543* | (2006.01) |
| *G01N 33/575* | (2026.01) |
| *G01N 33/58* | (2006.01) |

(52) U.S. Cl.
CPC ..... *G01N 33/57545* (2026.01); *G01N 21/763* (2013.01); *G01N 33/54326* (2013.01); *G01N 33/5759* (2026.01); *G01N 33/58* (2013.01)

(58) Field of Classification Search
CPC ........... G01N 33/57449; G01N 21/763; G01N 33/54326; G01N 33/57492; G01N 33/58; G01N 33/57488; G01N 33/5076; G01N 33/532; G01N 33/533
See application file for complete search history.

(56) References Cited

U.S. PATENT DOCUMENTS

| | | |
|---|---|---|
| 2014/0295426 A1 | 10/2014 | Albelda et al. |
| 2019/0219578 A1 | 7/2019 | Mitsuhashi |

FOREIGN PATENT DOCUMENTS

| | | |
|---|---|---|
| WO | WO-2017087940 A1 | 5/2017 |
| WO | WO-2019/094692 A2 | 5/2019 |

OTHER PUBLICATIONS

Yu et al. Beyond antibodies as binding partners: the role of antibody mimetics in bioanalysis. Annur. Rev. Anal. Chem 10:293-320, published Mar. 24, 2017.*
Shih et al. Development of a magnetic bead-based method for the collection of circulating extracellular vesicles (New Biotechnology 33(1): 116-122, Jan. 25, 2016.*
Search Report and Written Opinion for Application No. PCT/US20/64576, mailed Mar. 11, 2021.
Yang et al., "A Multifunctional Platform for Rapid Detection and Post Detection Analysis of Circulating Tumor Cells", The FASEB Journal Special Issue: Experimental Biology Meeting Abstracts. Oct. 2018. vol 31. No. S1, Abstract.
Nakai et al., A novel affinity-based method for the isolation of highly purified extracellular vesicles, Scientific Reports, 6(1): 33935, (Sep. 2016).
Jia, Yuan et al., "Microfluidic Approaches Toward the Isolation and Detection of Exosome Nanvesicles", IEEE Access, vol. 7; pp. 45080-45098 (2019).
Wang, Zhile et al., "Screening and multiple detection of cancer exosomes using an SERS-based method", Nanoscale, 10(19):9053-62 (2018).
Kabe, Yasuaki et al., "Application of high-performance magnetic nanobeads to biological sending devices", Analytical and Bioanalytical Chemistry, 411(9):1825-37 (2019).
Cheung, Nan et al., "Recent Advances in Biosensors for Detecting Cancer-Derived Exosomes", Trends in Biotechnology, 37(11):1236-1254 (Nov. 2019).
Kabe et al., "Development of a Highly Sensitive Device for Counting the Number of Disease-Specific Exosomes in Human Sera", Clinical Chemistry, 64(10):1463-1473 (2018).
Yuan et al., "Microfluidic Approaches Toward the Isolation and Detection of Exosome Nanvesicles", IEEE Access, vol. 7; pp. 45080-45098 (2019).
Zhile et al., "Screening and multiple detection of cancer exosomes using an SERS-based method", Nanoscale, 10(19):9053-62 (2018).
Yasuaki et al., "Application of high-performance magnetic nanobeads to biological sending devices", Analytical and Bioanalytical Chemistry, 411(9):1825-37 (2019).
Nan et al., "Recent Advances in Biosensors for Detecting Cancer-Derived Exosomes", Trends in Biotechnology, 37(11):1236-1254 (Nov. 2019).

(Continued)

*Primary Examiner* — Alana Harris Dent
(74) *Attorney, Agent, or Firm* — MARSHALL, GERSTEIN & BORUN LLP

(57) ABSTRACT

Described herein is a method for detecting the presence of circulating extracellular vesicles in a subject. The method comprises contacting a biological sample from the subject with an antibody mimetic that specifically binds to a cell surface marker on the vesicles, wherein the antibody mimetic is coupled to a detectable label; and detecting presence of extracellular vesicles in the sample by detecting the presence of the detectable label coupled to the antibody mimetic bound to the vesicles.

12 Claims, 2 Drawing Sheets

Specification includes a Sequence Listing.

(56) References Cited

OTHER PUBLICATIONS

Kabe et al., "Development of a Highly Sensitive Device for Counting the No. of Disease-Specific Exosomes in Human Sera", Clinical Chemistry, 64(10):1463-1473 (2018).

Koga et al., "Purification, Characterization and Biological Significance of Tumor-derived Exosomes", Anticancer Research, 25(6A):3703-3707 (2005).

Yang et al., "Bioluminescence: An Old Tool for New Applications Detection of Circulating Tumor Cells and Image-guided Therapy", PhD diss, University of Miami (2018).

Examination Report, European Patent Application No. 20900625.3, Mailing date Aug. 8, 2025, 7 pages.

* cited by examiner

SEQUENCE LISTING

<160> NUMBER OF SEQ ID NOS: 2

<210> SEQ ID NO 1
<211> LENGTH: 1545
<212> TYPE: PRT
<213> ORGANISM: Homo Sapiens

<400> SEQUENCE: 1

```
Gly Ala Cys Cys Thr Gly Gly Gly Thr Ala Ala Ala Ala Ala Cys
1               5                   10                  15

Thr Gly Cys Thr Gly Gly Ala Ala Gly Cys Gly Gly Cys Thr Cys Gly
            20                  25                  30

Thr Gly Cys Thr Gly Gly Thr Cys Ala Ala Gly Ala Thr Gly Ala Thr
        35                  40                  45

Gly Ala Ala Gly Thr Gly Cys Gly Thr Ala Thr Cys Cys Thr Gly Ala
    50                  55                  60

Thr Gly Gly Cys Thr Ala Ala Thr Gly Gly Thr Gly Cys Thr Gly Ala
65                  70                  75                  80

Thr Gly Thr Gly Ala Ala Cys Gly Cys Gly Ala Ala Ala Gly Ala Thr
                85                  90                  95

Thr Thr Thr Thr Ala Thr Gly Gly Cys Ala Thr Thr Ala Cys Cys Cys
            100                 105                 110

Cys Gly Cys Thr Gly Cys Ala Thr Cys Thr Gly Gly Cys Ala Gly Cys
            115                 120                 125

Ala Gly Cys Ala Thr Ala Cys Gly Gly Thr Cys Ala Cys Cys Thr Gly
    130                 135                 140

Gly Ala Ala Ala Thr Cys Gly Thr Gly Gly Ala Ala Gly Thr Thr Cys
145                 150                 155                 160

Thr Gly Cys Thr Gly Ala Ala Ala Cys Ala Thr Gly Gly Cys Gly Cys
            165                 170                 175

Gly Gly Ala Thr Gly Thr Gly Ala Ala Cys Gly Cys Cys Cys Ala Cys
            180                 185                 190

Gly Ala Cys Thr Gly Gly Ala Ala Thr Gly Gly Thr Thr Gly Gly Ala
            195                 200                 205

Cys Gly Cys Cys Gly Cys Thr Gly Cys Ala Thr Cys Thr Gly Gly Cys
    210                 215                 220

Thr Gly Cys Gly Ala Ala Ala Thr Ala Thr Gly Gly Cys Cys Ala Cys
225                 230                 235                 240

Cys Thr Gly Gly Ala Ala Ala Thr Thr Gly Thr Cys Gly Ala Ala Gly
            245                 250                 255

Thr Gly Cys Thr Gly Cys Thr Gly Ala Ala Ala Cys Ala Thr Gly Gly
            260                 265                 270

Cys Gly Cys Ala Gly Ala Thr Gly Thr Thr Ala Ala Cys Gly Cys Thr
    275                 280                 285

Ala Thr Cys Gly Ala Cys Ala Ala Thr Gly Cys Gly Gly Gly Thr Ala
    290                 295                 300

Ala Ala Ala Cys Cys Cys Cys Gly Cys Thr Gly Cys Ala Cys Cys Thr
305                 310                 315                 320

Gly Gly Cys Ala Gly Cys Ala Gly Cys Thr Cys Ala Thr Gly Gly Thr
            325                 330                 335

Cys Ala Cys Cys Thr Gly Gly Ala Ala Ala Thr Thr Gly Thr Thr Gly
            340                 345                 350

Ala Ala Gly Thr Cys Cys Thr Gly Cys Thr Gly Ala Ala Ala Thr Ala
    355                 360                 365
```

```
Cys Gly Gly Cys Gly Cys Cys Gly Ala Thr Gly Thr Cys Ala Ala Cys
    370             375                 380

Gly Cys Ala Cys Ala Gly Gly Ala Cys Ala Ala Ala Thr Thr Thr Gly
385                 390                 395                 400

Gly Thr Ala Ala Ala Ala Cys Gly Gly Cys Thr Thr Thr Cys Gly Ala
                405                 410                 415

Thr Ala Thr Thr Ala Gly Cys Ala Thr Cys Gly Ala Cys Ala Ala Cys
            420                 425                 430

Gly Gly Cys Ala Ala Thr Gly Ala Ala Gly Ala Thr Cys Thr Gly Gly
            435                 440                 445

Cys Cys Gly Ala Ala Ala Thr Cys Cys Thr Gly Cys Ala Ala Ala Ala
    450                 455                 460

Ala Cys Thr Gly Gly Gly Thr Gly Gly Cys Gly Gly Thr Gly Gly Cys
465                 470                 475                 480

Ala Gly Cys Cys Gly Thr Ala Gly Cys Gly Ala Cys Cys Thr Gly Gly
                485                 490                 495

Gly Thr Ala Ala Ala Ala Ala Ala Cys Thr Gly Cys Thr Gly Gly Ala
            500                 505                 510

Ala Gly Cys Thr Gly Cys Thr Cys Gly Thr Gly Cys Gly Gly Gly Thr
            515                 520                 525

Cys Ala Ala Gly Ala Thr Gly Ala Thr Gly Ala Ala Gly Thr Gly Cys
    530                 535                 540

Gly Thr Ala Thr Thr Cys Thr Gly Ala Thr Gly Gly Cys Thr Ala Ala
545                 550                 555                 560

Cys Gly Gly Thr Gly Cys Cys Gly Ala Thr Gly Thr Cys Ala Ala Thr
                565                 570                 575

Gly Cys Gly Ala Ala Ala Gly Ala Thr Gly Ala Ala Thr Ala Thr Gly
            580                 585                 590

Gly Cys Cys Thr Gly Ala Cys Cys Cys Cys Gly Cys Thr Gly Thr Ala
            595                 600                 605

Cys Cys Thr Gly Gly Cys Ala Ala Cys Gly Gly Cys Thr Cys Ala Thr
    610                 615                 620

Gly Gly Thr Cys Ala Cys Cys Thr Gly Gly Ala Ala Ala Thr Thr Gly
625                 630                 635                 640

Thr Gly Gly Ala Ala Gly Thr Thr Cys Thr Gly Cys Thr Gly Ala Ala
            645                 650                 655

Ala Ala Ala Cys Gly Gly Cys Gly Cys Ala Gly Ala Thr Gly Thr Cys
            660                 665                 670

Ala Ala Thr Gly Cys Gly Gly Thr Gly Gly Ala Cys Gly Cys Cys Ala
            675                 680                 685

Thr Cys Gly Gly Thr Thr Thr Ala Cys Cys Cys Cys Gly Cys Thr
    690                 695                 700

Gly Cys Ala Thr Cys Thr Gly Gly Cys Gly Gly Cys Cys Thr Thr Cys
705                 710                 715                 720

Ala Thr Thr Gly Gly Cys Cys Ala Cys Cys Thr Gly Gly Ala Ala Ala
            725                 730                 735

Thr Cys Gly Cys Gly Gly Ala Ala Gly Thr Thr Cys Thr Gly Cys Thr
            740                 745                 750

Gly Ala Ala Ala Cys Ala Thr Gly Gly Cys Gly Cys Ala Gly Ala Thr
            755                 760                 765

Gly Thr Cys Ala Ala Cys Gly Cys Thr Cys Ala Gly Gly Ala Cys Ala
    770                 775                 780

Ala Ala Thr Thr Thr Gly Gly Thr Ala Ala Ala Ala Cys Gly Gly Cys
```

```
785                 790                 795                 800

Gly Thr Thr Cys Gly Ala Thr Ala Thr Thr Ala Gly Cys Ala Thr Cys
                805                 810                 815

Gly Gly Cys Ala Ala Cys Gly Gly Thr Ala Ala Thr Gly Ala Ala Gly
                820                 825                 830

Ala Cys Cys Thr Gly Gly Cys Cys Gly Ala Ala Ala Thr Thr Cys Thr
                835                 840                 845

Gly Cys Ala Ala Ala Ala Ala Cys Thr Gly Gly Thr Gly Gly Cys
850                 855                 860

Gly Gly Thr Thr Cys Thr Gly Gly Thr Gly Gly Cys Gly Gly Thr Ala
865                 870                 875                 880

Gly Cys Gly Gly Cys Gly Gly Thr Gly Gly Cys Ala Gly Thr Ala Thr
                885                 890                 895

Gly Ala Ala Ala Cys Cys Gly Ala Cys Cys Gly Ala Ala Ala Ala Thr
                900                 905                 910

Ala Ala Thr Gly Ala Ala Gly Ala Cys Thr Thr Ala Ala Cys Ala
                915                 920                 925

Thr Cys Gly Thr Gly Gly Cys Ala Gly Thr Gly Gly Cys Gly Ala Gly
                930                 935                 940

Thr Ala Ala Cys Thr Thr Thr Gly Cys Thr Ala Ala Gly Ala Cys Cys
945                 950                 955                 960

Gly Ala Cys Cys Thr Gly Gly Ala Cys Gly Cys Thr Gly Ala Cys Cys
                965                 970                 975

Gly Thr Gly Gly Thr Ala Ala Ala Cys Thr Gly Cys Cys Gly Gly Gly
                980                 985                 990

Cys Ala Ala Ala Ala Ala Ala Cys  Thr Gly Cys Cys Gly  Cys Thr Gly
        995                 1000                 1005

Gly Ala  Ala Gly Thr Thr Cys  Thr Gly Ala Ala Ala  Gly Ala Ala
    1010                 1015                 1020

Ala Thr  Thr Gly Ala Ala Gly  Cys Ala Ala Ala Cys  Gly Cys Ala
    1025                 1030                 1035

Cys Gly  Thr Ala Ala Ala Gly  Cys Ala Gly Gly Thr  Thr Gly Cys
    1040                 1045                 1050

Ala Cys  Cys Cys Gly Thr Gly  Gly Thr Thr Gly Cys  Cys Thr Gly
    1055                 1060                 1065

Ala Thr  Cys Thr Gly Thr Cys  Thr Gly Ala Gly Cys  Cys Ala Thr
    1070                 1075                 1080

Ala Thr  Cys Ala Ala Ala Thr  Gly Cys Ala Cys Gly  Cys Cys Gly
    1085                 1090                 1095

Ala Ala  Ala Ala Thr Gly Ala  Ala Ala Ala Ala  Thr Gly Gly
    1100                 1105                 1110

Cys Thr  Cys Cys Cys Gly Gly  Gly Cys Cys Gly Thr  Thr Gly Thr
    1115                 1120                 1125

Cys Ala  Cys Ala Cys Cys Thr  Ala Thr Gly Ala Ala  Gly Gly Thr
    1130                 1135                 1140

Gly Ala  Thr Ala Ala Ala Gly  Ala Ala Thr Cys Thr  Gly Cys Ala
    1145                 1150                 1155

Cys Ala  Gly Gly Gly Cys Gly  Gly Thr Ala Thr Thr  Gly Gly Cys
    1160                 1165                 1170

Gly Ala  Ala Gly Cys Thr Ala  Thr Thr Gly Thr Cys  Gly Ala Thr
    1175                 1180                 1185

Ala Thr  Cys Cys Cys Gly Gly  Ala Ala Ala Thr Thr  Cys Cys Gly
    1190                 1195                 1200
```

```
Gly Gly  Thr Thr Thr Thr Ala  Ala Ala Gly Ala Cys  Cys Thr Gly
    1205            1210            1215

Gly Ala  Ala Cys Cys Gly Ala  Thr Ala Gly Ala Ala  Cys Ala Gly
    1220            1225            1230

Thr Thr  Cys Ala Thr Cys Gly  Cys Gly Cys Ala Ala  Gly Thr Gly
    1235            1240            1245

Gly Ala  Thr Cys Thr Gly Thr  Gly Cys Gly Thr Thr  Gly Ala Cys
    1250            1255            1260

Thr Gly  Thr Ala Cys Cys Ala  Cys Gly Gly Gly Cys  Thr Gly Cys
    1265            1270            1275

Cys Thr  Gly Ala Ala Ala Gly  Gly Thr Cys Thr Gly  Gly Cys Cys
    1280            1285            1290

Ala Ala  Thr Gly Thr Gly Cys  Ala Gly Thr Gly Thr  Ala Gly Thr
    1295            1300            1305

Gly Ala  Cys Cys Thr Gly Cys  Thr Gly Ala Ala Ala  Ala Ala Ala
    1310            1315            1320

Thr Gly  Gly Cys Thr Gly Cys  Cys Gly Cys Ala Ala  Cys Gly Cys
    1325            1330            1335

Thr Gly  Thr Gly Cys Thr Ala  Cys Gly Thr Thr Cys  Gly Cys Ala
    1340            1345            1350

Ala Gly  Cys Ala Ala Ala Ala  Thr Thr Cys Ala Gly  Gly Gly Thr
    1355            1360            1365

Cys Ala  Ala Gly Thr Gly Gly  Ala Cys Ala Ala Ala  Ala Thr Cys
    1370            1375            1380

Ala Ala  Ala Gly Gly Thr Gly  Cys Ala Gly Gly Thr  Gly Gly Thr
    1385            1390            1395

Gly Ala  Thr Ala Gly Cys Cys  Thr Gly Ala Gly Cys  Ala Cys Cys
    1400            1405            1410

Cys Cys  Gly Cys Cys Gly Ala  Cys Cys Cys Cys Gly  Ala Gly Cys
    1415            1420            1425

Cys Cys  Gly Ala Gly Cys Ala  Cys Cys Cys Cys Gly  Cys Cys Gly
    1430            1435            1440

Gly Gly  Cys Gly Gly Thr Thr  Gly Cys Gly Gly Thr  Gly Gly Cys
    1445            1450            1455

Thr Gly  Thr Gly Gly Thr Gly  Gly Thr Thr Gly Cys  Gly Gly Cys
    1460            1465            1470

Gly Gly  Cys Thr Gly Thr Ala  Gly Cys Cys Thr Gly  Gly Ala Ala
    1475            1480            1485

Gly Gly  Thr Ala Cys Cys Ala  Thr Gly Ala Gly Cys  Gly Gly Cys
    1490            1495            1500

Cys Thr  Gly Ala Ala Cys Gly  Ala Thr Ala Thr Thr  Thr Thr Thr
    1505            1510            1515

Gly Ala  Ala Gly Cys Gly Cys  Ala Gly Ala Ala Ala  Ala Thr Thr
    1520            1525            1530

Gly Ala  Ala Thr Gly Gly Cys  Ala Thr Gly Ala Ala
    1535            1540            1545
```

<210> SEQ ID NO 2
<211> LENGTH: 514
<212> TYPE: PRT
<213> ORGANISM: Homo Sapiens
<400> SEQUENCE: 2

```
Asp Leu Gly Lys Lys Leu Leu Glu Ala Ala Arg Ala Gly Gln Asp Asp
```

```
1                   5                   10                  15

Glu Val Arg Ile Leu Met Ala Asn Gly Ala Asp Val Asn Ala Lys Asp
                20              25              30

Phe Tyr Gly Ile Thr Pro Leu His Leu Ala Ala Ala Tyr Gly His Leu
                35              40              45

Glu Ile Val Glu Val Leu Leu Lys His Gly Ala Asp Val Asn Ala His
    50              55              60

Asp Trp Asn Gly Trp Thr Pro Leu His Leu Ala Ala Lys Tyr Gly His
65              70              75              80

Leu Glu Ile Val Glu Val Leu Leu Lys His Gly Ala Asp Val Asn Ala
                85              90              95

Ile Asp Asn Ala Gly Lys Thr Pro Leu His Leu Ala Ala Ala His Gly
                100             105             110

His Leu Glu Ile Val Glu Val Leu Leu Lys Tyr Gly Ala Asp Val Asn
                115             120             125

Ala Gln Asp Lys Phe Gly Lys Thr Ala Phe Asp Ile Ser Ile Asp Asn
    130             135             140

Gly Asn Glu Asp Leu Ala Glu Ile Leu Gln Lys Leu Gly Gly Gly Gly
145             150             155             160

Ser Arg Ser Asp Leu Gly Lys Lys Leu Glu Ala Ala Arg Ala Gly Gln
                165             170             175

Asp Asp Glu Val Arg Ile Leu Met Ala Asn Gly Ala Asp Val Asn Ala
                180             185             190

Lys Asp Glu Tyr Gly Leu Thr Pro Leu Tyr Leu Ala Thr Ala His Gly
                195             200             205

His Leu Glu Ile Val Glu Val Leu Leu Lys Asn Gly Ala Asp Val Asn
    210             215             220

Ala Val Asp Ala Ile Gly Phe Thr Pro Leu His Leu Ala Ala Phe Ile
225             230             235             240

Gly His Leu Glu Ile Ala Glu Val Leu Leu Lys His Gly Ala Asp Val
                245             250             255

Asn Ala Gln Asp Lys Phe Gly Lys Thr Ala Phe Asp Ile Ser Ile Gly
                260             265             270

Asn Gly Asn Glu Asp Leu Ala Glu Ile Leu Gln Lys Leu Gly Gly Gly
                275             280             285

Ser Gly Gly Gly Ser Gly Gly Gly Ser Met Lys Pro Thr Glu Asn Asn
    290             295             300

Glu Asp Phe Asn Ile Val Ala Val Ala Ser Asn Phe Ala Thr Thr Asp
305             310             315             320

Leu Asp Ala Asp Arg Gly Lys Leu Pro Gly Lys Lys Leu Pro Leu Glu
                325             330             335

Val Leu Lys Glu Ile Glu Ala Asn Ala Arg Lys Ala Gly Cys Thr Arg
                340             345             350

Gly Cys Leu Ile Cys Leu Ser His Ile Lys Cys Thr Pro Lys Met Lys
                355             360             365

Lys Trp Leu Pro Gly Arg Cys His Thr Tyr Glu Gly Asp Lys Glu Ser
    370             375             380

Ala Gln Gly Gly Ile Gly Glu Ala Ile Val Asp Ile Pro Glu Ile Pro
385             390             395             400

Gly Phe Lys Asp Leu Glu Pro Ile Glu Gln Phe Ile Ala Gln Val Asp
                405             410             415

Leu Cys Val Asp Cys Thr Thr Gly Cys Leu Lys Gly Leu Ala Asn Val
                420             425             430
```

-continued

```
Gln Cys Ser Asp Leu Leu Lys Lys Trp Leu Pro Gln Arg Cys Ala Thr
        435             440             445

Phe Ala Ser Lys Ile Gln Gly Gln Val Asp Lys Ile Lys Gly Ala Gly
    450             455             460

Gly Asp Ser Leu Ser Thr Pro Pro Thr Pro Ser Pro Ser Thr Pro Pro
465             470             475             480

Gly Gly Cys Gly Gly Cys Gly Gly Cys Gly Gly Cys Ser Leu Glu Gly
            485             490             495

Thr Met Ser Gly Leu Asn Asp Ile Phe Glu Ala Gln Lys Ile Glu Trp
            500             505             510

His Glu
```

MATERIALS AND METHODS FOR EXTRACELLULAR VESICLE DETECTION

CROSS-REFERENCE TO RELATED APPLICATIONS

The present application claims the benefit of priority to U.S. Provisional Application No. 62/947,149, filed Dec. 12, 2019, the disclosure of which is incorporated herein by reference in its entirety.

BACKGROUND

Extracellular vesicles (EVs) are cell-derived vesicles with a closed double-layer membrane structure. They carry various molecules (proteins, lipids, and RNAs) on their surface as well as in the lumen. Exosomes and other EVs play a critical role in intercellular communication and cellular content transfer, e.g. mRNAs and microRNAs, in both physiological and pathological settings, such as tumor development and progression. Approaches to detect and characterize exosomes and other EVs may include: (1) electron microscopy (EM) to assess structure and size; (2) nanoparticle tracking analysis (NTA) to reveal size and zeta potential; (3) protein analysis via immunofluorescence staining, western blotting, ELISA, and mass spectrometry, (4) RNA analysis using array platforms, RNA sequencing, and PCR, and (5) analysis of lipids, sugar, and other components by biochemical assays.

Despite the high clinical value of these vesicles, establishment of the clinical utility of EVs to improve cancer management has been challenging. Tumor-derived EVs relative to those originating from normal tissues are scarce in circulation. Furthermore, it is difficult to separate them from bulk EVs due to the similarity of physical and biological properties, resulting in low recovery yield and purity. These drawbacks have significant negative effects on the sensitivity of EV detection and the interpretation of molecular profiling of their contents in early prognosis of ovarian cancer. Thus, development of highly sensitive assays that enable detection of rare tumor-derived EVs in body fluids and isolation of those vesicles for molecular analysis is highly desirable.

SUMMARY

In one aspect, described herein is a method for detecting the presence of circulating extracellular vesicles in a subject, the method comprising (a) contacting a biological sample from the subject with an antibody mimetic that specifically binds to a cell surface marker on the vesicles, wherein the antibody mimetic is coupled to a detectable label; (b) detecting presence of extracellular vesicles in the sample by detecting the presence of the detectable label coupled to the antibody mimetic bound to the vesicles.

In some embodiments, the extracellular vesicles are tumor-derived extracellular vesicles. In some embodiments, the extracellular vesicles are exosomes or microvesicles or a combination thereof. In some embodiments, the tumor-derived extracellular vesicles are ovarian tumor-derived extracellular vesicles.

In some embodiments, the antibody mimetic specifically binds a cell surface marker selected from the group consisting of EpCAM, EGFR, HER2, c-MET, and Claudin-4.

The method optionally comprises contacting the biological sample with an antibody mimetic that specifically binds EpCAM, an antibody mimetic that specifically binds EGFR, and an antibody mimetic that specifically binds HER2. In some embodiments, the method comprises contacting the biological sample with an antibody mimetic that specifically binds EpCAM, an antibody mimetic that specifically binds EGFR, an antibody mimetic that specifically binds HER2, an antibody mimetic that specifically binds c-MET, and an antibody mimetic that specifically binds Claudin-4.

In some embodiments, the biological sample is serum or plasma.

In some embodiments, the detectable label comprises a bioluminescent protein.

In some embodiments, the method further comprises isolating the detected extracellular vesicles from the biological sample. In some embodiments, the antibody mimetic-detectable label conjugate is biotinylated and the isolating step comprises contacting the detected extracellular vesicles with streptavidin magnetic beads.

In the some embodiments, the method comprises, prior to step (a), isolating extracellular vesicles from serum or plasma from the subject to prepare the biological sample. In some embodiments, isolating the extracellular vesicles from serum or plasma comprises applying magnetic particles coated with phosphatidylserine binding proteins to the serum or plasma and removing extracellular vesicle-bound magnetic particles from the serum or plasma.

In another aspect, described herein is a method of diagnosing ovarian cancer in a subject comprising (a) contacting a biological sample with an antibody mimetic that specifically binds to cell surface marker expressed on ovarian tumor-derived extracellular vesicles, wherein the antibody mimetic is coupled to a detectable label; and (b) detecting presence of the ovarian tumor-derived extracellular vesicles in the sample by detecting the presence of the label coupled to the antibody mimetic bound to the vesicles.

DETAILED DESCRIPTION

Figure 1:
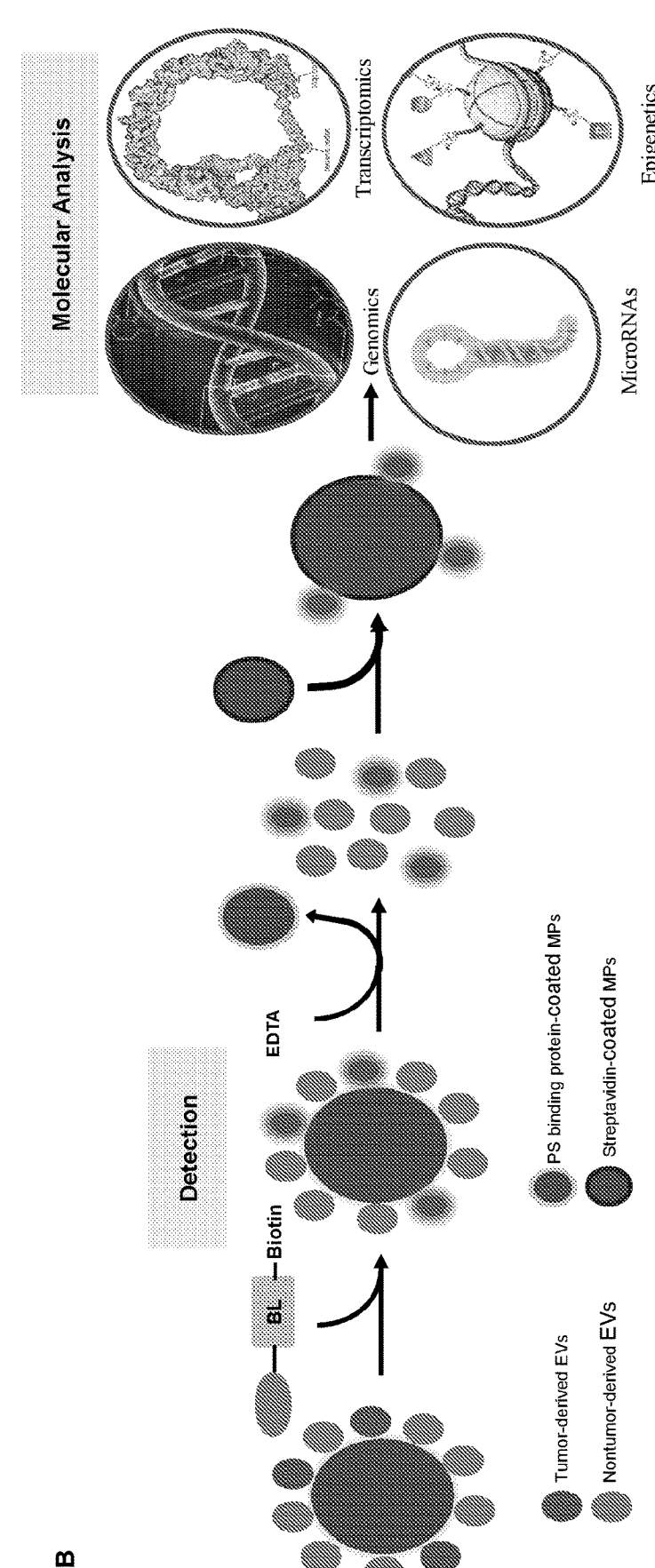
FIG. 1A is a schematic diagram of a fusion protein comprising an antibody mimetic (AM), a bioluminescence protein (BL) and biotin.
FIG. 1B is a schematic of the assay described in the Example. Bulk EVs from serum/plasma of cancer patients are captured by using magnetic particles (MPs) coated with phosphatidylserine (PS) binding proteins. PS is a universal marker of EVs. A cocktail of fusion proteins are used to detect tumor-derived EVs from bulk EVs. Bulk EVs are released from MPs by EDTA. Streptavidin-coated MPs are used to capture tumor-derived EVs labeled with fusion proteins. Molecular analyses of the enriched tumor-derived EVs are performed to identify molecular defects associated with cancer progression. While this description relates to an aspect of the disclosure involving cancer cells, it will be appreciated that the assay may be used to detect extracellular vesicles associated with other disorders.

In one aspect, described herein is a method for detecting the presence of circulating extracellular vesicles in a subject comprising contacting a biological sample from the subject with an antibody mimetic that specifically binds to a cell surface marker (e.g., a cancer-specific cell-surface marker) on the vesicles. The antibody mimetic is coupled to a detectable label. The method further comprises detecting the presence of extracellular vesicles in the sample by detecting the presence of the detectable label coupled to the antibody mimetic bound to the vesicles.

Extracellular Vesicles

Extracellular vesicles are small lipid membrane enclosed vesicles that are released into the extracellular environment from a variety of different cells such as, but not limited to, cells that originate from, or are derived from, the ectoderm, endoderm, or mesoderm, including any such cells that have undergone genetic, environmental, and/or any other variations or alterations (e.g. tumor cells, bacterial/virally infected cells, or cells with genetic mutations). In some embodiments, the extracellular vesicles are secreted from tumor cells.

Extracellular vesicles may include, for example, circulating microvesicles (cMVs), microvesicles, exosomes, nanovesicles, dexosomes, blebs, blebby, prostasomes, microparticles, intralumenal vesicles, membrane fragments, intralumenal endosomal vesicles, endosomal-like vesicles, exocytosis vehicles, endosome vesicles, endosomal vesicles, apoptotic bodies, multivesicular bodies, secretory vesicles, phospholipid vesicles, liposomal vesicles, argosomes, texasomes, secresomes, tolerosomes, melanosomes, oncosomes, or exocytosed vehicles.

An exosome is typically created intracellularly when a segment of the cell membrane spontaneously invaginates and is ultimately exocytosed. As used herein, exosomes can also include any shed membrane bound particle that is derived from either the plasma membrane or an internal membrane. Exosomes can also include cell-derived structures bounded by a lipid bilayer membrane arising from both herniated evagination (blebbing) separation and sealing of portions of the plasma membrane. Exosomes can also arise from the export of any intracellular membrane-bounded vesicular structure containing various membrane-associated proteins, including surface-bound molecules derived from the host circulation that bind selectively to the exosomal proteins together with molecules contained in the exosome lumen (e.g., including but not limited to mRNAs, microRNAs or intracellular proteins). Blebs and blebbing are further described in Charras et al, Nature Reviews Molecular and Cell Biology, Vol. 9, No. 9, p. 730-736 (2008). Exosomes can also include membrane fragments.

Extracellular vesicles, and in particular, exosomes, may have, but not be limited to, a diameter of greater than about 10, greater than about 20, or greater than about 30 nm. In some embodiments, the exosomes have, but are not limited to, a diameter of less than about 1000 nm, less than about 800 nm, less than about 500 nm, less than about 200 nm, less than about 100 nm, or less than about 50 nm (optionally with a lower limit of 20 nm). For example, the extracellular vesicles can have a diameter of about 30-1000 nm, about 30 to about 800 nm, about 30 to about 200 nm, about 30 to about 100 nm, about 20 nm to about 100 nm, about 30 nm to about 150 nm, about 30 nm to about 120 nm, about 50 nm to about 150 nm, or about 50 nm to about 120 nm. As used throughout, the term "about," when referring to a value or to an amount, is meant to encompass variations in some embodiments of ±10% from the specified amount, where such variations are appropriate.

In some embodiments, the extracellular vesicle is a tumor-derived extracellular vesicle.

The methods described herein can be used for the detection, diagnosis, targeting and treatment of a subject having a disorder, such as cancer, including solid tumor cancers, hematologic cancers and metastatic cancers. The terms "cancer," "tumor" and "cancerous" refer to or describe the physiological condition in mammals in which a population of cells are characterized by unregulated cell growth. A cancer may be a non-solid tumor type or a solid tumor. Examples of cancer include, but are not limited to, carcinoma, lymphoma, blastoma, sarcoma, and leukemia. In some embodiments, the cancer is breast cancer, prostate cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, colon cancer, colorectal cancer, gastric cancer, endometrial or uterine carcinoma, salivary gland carcinoma, kidney cancer, liver cancer, vulval cancer, thyroid cancer, hepatic carcinoma and various types of head and neck cancer, hematologic malignancies, acute myeloid leukemia, lymphoma and leukemia, metastases of the pancreas, breast, lung, colon or melanoma.

In some embodiments, the tumor-derived extracellular derived vesicles are ovarian tumor-derived extracellular vesicles.

Antibody Mimetics

The antibody mimetic specifically binds a cell surface marker, i.e., in some embodiments, the antibody mimetic specifically binds a cell surface marker selected from the group consisting of EpCAM (Genbank Accession No. NP_002345; EGFR (Genbank Accession No. AAI18666.1), HER2 (UniProt/SwissProt Accession No. P04626), c-MET (UniProt/SwissProt Accession No. P08581, and Claudin-4 (Genbank Accession No. NP_001296). Any combination of mimetics that bind EpCAM, EGFR, HER2, c-MET, and Claudin-4 may be used. In some embodiments, the method comprises contacting the biological sample with an antibody mimetic that specifically binds EpCAM, an antibody mimetic that specifically binds EGFR and an antibody mimetic that specifically binds Her2. In some embodiments, the method comprises contacting the biological sample with an antibody mimetic that specifically binds EpCAM, an antibody mimetic that specifically binds EGFR, an antibody mimetic that specifically binds HER2, an antibody mimetic that specifically binds c-MET, and an antibody mimetic that specifically binds Claudin-4.

The term "antibody mimetic" refers to organic compounds that, like antibodies, can specifically bind antigens, but that are not structurally related to antibodies. Antibody mimetics are artificial peptides or proteins typically with a molar mass of about 3 to 20 kDa. Non-limiting examples of antibody mimetics are affibodies, affilins, affimers, affitins, alphabodies, anticalins, avimers, DARPins, fynomers, Kunitz domain peptides, monobodies, or synthetic or non-synthetic peptide ligands, e.g. from a (random) peptide library.

In some embodiments, the antibody mimetic is an affibody molecule. An affibody molecule comprises a protein scaffold comprising one or more alpha helices without any disulfide bridges. In some embodiments, the affibody molecule comprises one, two or three alpha helices.

In some embodiments, the antibody mimetic is an affilin molecule. An affilin molecule comprises a protein scaffold produced by modification of exposed amino acids of, for example, either gamma-B crystallin or ubiquitin. Affilin molecules functionally mimic an antibody's affinity to antigen, but do not structurally mimic an antibody. In any protein scaffold used to make an affilin, amino acids that are accessible to solvent or possible binding partners in a properly-folded protein molecule are considered exposed amino acids. Any one or more of these exposed amino acids may be modified to specifically bind to a target sequence or antigen.

In some embodiments, the antibody mimetic is an affimer molecule. An affimer molecule comprises a protein scaffold comprising a highly stable protein engineered to display peptide loops that provide a high affinity binding site for a specific target sequence. Exemplary affimer molecules comprise a protein scaffold based upon a cystatin protein or tertiary structure thereof. Exemplary affimer molecules of the disclosure may share a common tertiary structure of comprising an alpha-helix lying on top of an anti-parallel beta-sheet.

In some embodiments, the antibody mimetic is an affitin molecule. An affitin molecule comprises an artificial protein scaffold, the structure of which may be derived, for example, from a DNA binding protein. Affitins selectively bind a target sequence, which may be the entirety or part of an antigen. Exemplary affitins are manufactured by randomizing one or more amino acid sequences on the binding surface of a DNA binding protein and subjecting the resultant protein to ribosome display and selection. Target sequences of affitins may be found, for example, in the genome or on the surface of a peptide, protein, virus, or bacteria.

In some embodiments, the antibody mimetic is an alpha-body molecule. In some embodiments, an alphabody molecule comprises a small protein (typically of less than 10 kDa) that bind to a variety of target sequences (including antigens). Alphabody molecules are capable of reaching and binding to intracellular target sequences. Structurally, alphabody molecules comprise an artificial sequence forming single chain alpha helix (similar to naturally occurring coiled-coil structures). In some embodiments, alphabody molecules comprise a protein scaffold comprising one or more amino acids that are modified to specifically bind target proteins. Regardless of the binding specificity of the molecule, alphabody molecules of the disclosure maintain correct folding and thermostability.

In some embodiments, the antibody mimetic is an anti-calin molecule. Anticalin molecules comprise artificial proteins that bind to target sequences or sites in either proteins or small molecules. Anticalin molecules may comprise an artificial protein derived from a human lipocalin. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules typically comprise a barrel structure comprising antiparallel beta-strands pairwise connected by loops and an attached alpha helix.

In some embodiments, the antibody mimetic is an avimer molecule. An avimer molecule comprises an artificial protein that specifically binds to a target sequence (which may also be an antigen). Avimers may recognize multiple binding sites within the same target or within distinct targets. When an avimer recognizes more than one target, the avimer mimics the function of a bispecific antibody. The artificial protein avimer may comprise two or more peptide sequences of approximately 30-35 amino acids each. These peptides may be connected via one or more linker peptides.

In some embodiments, the antibody mimetic is a DARPin. DARPins (Designed Ankyrin Repeat Proteins) comprise genetically-engineered, recombinant, or chimeric proteins having high specificity and high affinity for a target sequence. In certain embodiments, DARPins are derived from ankyrin proteins and, optionally, comprise at least three repeat motifs (also referred to as repetitive structural units) of the ankyrin protein. Ankyrin proteins mediate high-affinity protein-protein interactions.

In some embodiments, the antibody mimetic is a fynomer. A fynomer comprises a small binding protein (about 7 kDa) derived from the human Fyn SH3 domain and engineered to bind to target sequences and molecules with equal affinity and equal specificity as an antibody.

In some embodiments, the antibody mimetic is a Kunitz domain peptide. Kunitz domain peptides comprise a protein scaffold comprising a Kunitz domain. Kunitz domains comprise an active site for inhibiting protease activity. Structurally, Kunitz domains comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

In some embodiments, the antibody mimetic is a monobody. Monobodies are small proteins (comprising about 94 amino acids and having a mass of about 10 kDa) comparable in size to a single chain antibody. These genetically engineered proteins specifically bind target sequences including antigens. Monobodies may specifically target one or more distinct proteins or target sequences.

Detectable Label

In some embodiments, a detectable label is coupled to the antibody mimetic. The particular label or detectable group used in the assay can be detectable by spectroscopic, photochemical, biochemical, immunochemical, electrical, optical or chemical means. Exemplary labels include, but are not limited to, magnetic beads (e.g. Dynabeads™) fluorescent dyes (e.g., fluorescein isothiocyanate, Texas red, rhodamine, and the like), radiolabels (e.g., $^3$H, $^{14}$C, $^{35}$S, $^{125}$I, $^{121}$I, $^{112}$In, $^{99}$mTc), other imaging agents such as microbubbles (for ultrasound imaging), $^{18}$F, $^{11}$C, $^{15}$O (for, e.g., Positron emission tomography), $^{99}$mTC, $^{111}$In (for, e.g., Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entireties. See also Handbook of Fluorescent Probes and Research Chemicals (6.sup.th Ed., Molecular Probes, Inc., Eugene Oreg.).

The label can be coupled directly or indirectly to the desired component of the assay according to methods well known in the art. As indicated above, a wide variety of labels can be used, with the choice of label depending on sensitivity required, ease of conjugation with the mimetic, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody mimetic.

The molecule can also be coupled directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, and the like. Chemiluminescent compounds include luciferin and 2,3-dihydrophthalazinediones, e.g., luminol. For a review of various labeling or signal producing systems suitable for use, see, U.S. Pat. No. 4,391,904, incorporated herein by reference in its entirety and for all purposes.

Any means of detecting labels may be used in the context of the disclosure. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally, simple calorimetric labels can be detected simply by observing the color associated with the label. Thus, in various dipstick assays, conjugated gold often appears pink, while various conjugated beads appear the color of the bead.

In some embodiments, the detection methods described herein comprise contacting a biological sample from the subject with an antibody mimetic that specifically binds to a cell surface marker on the vesicles, wherein the antibody mimetic is coupled to a detectable label, and detecting the presence of extracellular vesicles in the sample by detecting the presence of the detectable label coupled to the antibody mimetic bound to the vesicles.

Exosomes and other extracellular vesicles may be directly assayed from the biological sample, such that the level of exosomes is determined or the one or more cell surface markers of the exosomes are detected without prior isolation, purification, or concentration of the exosomes.

Alternatively, in some embodiments, exosomes may be purified or concentrated prior to analysis. Analysis can include quantitating the amount of one or more exosome populations within a biological sample. For example, a heterogeneous population of exosomes can be quantitated. Alternatively, a homogeneous population of exosomes, such as a population of exosomes with a particular cell surface marker profile or derived from a particular cell type (cell-of-origin specific exosomes) can be isolated from a heterogeneous population of exosomes and quantitated. Analysis of an exosome can also include detecting, quantitatively or qualitatively, a particular cell surface marker, of an exosome.

In some embodiments, the extracellular vesicle is detected in a biological sample of a subject. Exemplary biological samples include, but are not limited to, blood, serum, plasma, urine, peripheral blood, ascites, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. In various aspects, the biological sample is serum or plasma.

In some embodiments, the extracellular vesicles are isolated from the biological sample. Exosomes and other extracellular vesicles may be concentrated or isolated from a biological sample by any method including, but not limited to, size exclusion chromatography, density gradient centrifugation, differential centrifugation, nanomembrane ultrafiltration, immunoabsorbent capture, affinity purification, microfluidic separation, commercially available protein purification kits, or combinations thereof.

In some embodiments, the extracellular vesicles are isolated from the biological sample by a method comprising contacting the detected extracellular vesicles with streptavidin magnetic beads. In some embodiments, the method comprises isolating the extracellular vesicles from a biological sample (e.g., serum or plasma) by applying magnetic particles coated with phosphatidylserine binding proteins to the biological sample (e.g., serum or plasma) and removing extracellular vesicle-bound magnetic particles from the biological sample (e.g., serum or plasma).

Diagnostic/Therapeutic Methods

Also described herein is a method of diagnosing cancer in a subject comprising contacting a biological sample with an antibody mimetic that specifically binds to a cell surface marker expressed on tumor-derived extracellular vesicles, wherein the antibody mimetic is coupled to a detectable label; and detecting presence of the tumor-derived extracellular vesicles in the sample by detecting the presence of the label coupled to the antibody mimetic bound to the vesicles. In some embodiments, the tumor-derived extracellular vesicles are ovarian tumor-derived extracellular vesicles.

In some embodiments, the method of diagnosis or prognosis can be used to indicate or guide treatment of ovarian cancer or other cancers. For example, the method can further comprise the step of providing suitable treatment if the subject is identified as having ovarian tumor-specific extracellular vesicles. Suitable treatment can include the use of a variety of different methods of treating cancer, such as surgery, radiation therapy, and administration of hormonal or anticancer agents.

Surgery is often the preferred treatment for ovarian cancer. Surgery involves removal of or more parts of the female reproductive tract, including one (unilateral oophorectomy) or both ovaries (bilateral oophorectomy), the fallopian tubes (salpingectomy), the uterus (hysterectomy), and/or the omentum (omentectomy). Typically, if a subject is diagnosed with ovarian cancer, all of these are removed. However, for low-grade, unilateral stage IA cancers, only the involved ovary (which must be unruptured) and fallopian tube will be removed.

Another method of treating ovarian cancer is radiation therapy.

Other methods of treating ovarian cancer include administration of therapeutic agents such as hormonal or anticancer agents. Accordingly, in some embodiments, the method of treatment further comprises the step of administering or prescribing a therapeutic agent targeted to ovarian cancer to a subject diagnosed as having ovarian cancer. Administration of anticancer agents (i.e., chemotherapy) may be used after surgery to treat any residual disease, or may be performed first, followed by surgery. This is called "neoadjuvant chemotherapy," and is common when a tumor cannot be completely removed or optimally debulked via surgery. If a unilateral salpingo-oophorectomy or other surgery is performed, additional chemotherapy, called "adjuvant chemotherapy" can be given. Chemotherapies used in ovarian cancer include paclitaxel, cisplatin, topotecan, and gemcitabine. Ovarian cancer involving germ cell malignancies are treated differently using a regimen of bleomycin, etoposide, and cisplatin.

EXAMPLES

Conditioned medium were collected from cultured MCF-7 (Her2-Low expression) and BT474 (Her2-High expression) cancer cells respectively. After removing cell debris and apoptotic bodies, extracellular vesicles (EVs) were captured from the conditioned medium by using phosphatidylserine (PS) binding protein-coated magnetic particles (MPs). The Her-2-positive EVs were determined by using one or more anti-Her2 fusion protein constructs having the components set forth in FIG. 1A.

The DNA of the anti-Her2 fusion protein was synthesized and cloned into expression plasmid pColdI. The plasmids inserted with the gene with the fusion protein were co-transformed with plasmid pBirA into Shuffle express competent E. coli for protein expression. The bacterial cells were grown overnight at 37° C., 250 rpm in small culture (5 mL of LB broth containing 100 m/mL ampicillin). The small bacterial culture was inoculated into 500 mL of TB broth containing 100 m/mL ampicillin and incubated at 37° C., 250 rpm until OD600 reached around 1.0. The culture medium was cooled in an ice-water bath for over 1 hour and subsequently biotin and IPTG was added to the bacterial culture at the final concentration of 500 μM and 0.1 mM, respectively. After incubating 24 hours at 16° C., the cells were harvested by centrifugation at 7,000 g for 10 minutes and lysed in 10 mL of BugBuster reagent. The fusion proteins were purified using a column of Ni-NTA agarose. Briefly, cell debris from bacterial lysate was removed by centrifugation at 18,000 g for 20 minutes. Cell lysate were incubated with Ni-NTA agarose beads at room temperature for 1 hour. The beads were washed with 50 mM NaH2PO4, 300 mM NaCl, 20 mM imidazole, pH 8.0 buffer, and the fusion proteins were eluted with 50 mM NaH2PO4, 300 mM NaCl, 150 mM imidazole, pH 8.0 buffer. The fusion proteins were subjected to dialysis against PBS pH 7.4 to remove imidazole. MCF-7 and BT474 cancer cells were grown to 60-70% confluency in growth medium with 10% FBS and washed with PBS to remove growth medium completely. Later the cancer cells were incubated in growth medium with 10% exosome-depleted FBS at 37° C. for 24 hours. Conditioned medium were collected from cultured cancer cells. Cell debris and apoptotic bodies were removed by centrifugation in sequential steps (300 g for 5 minutes, 1,200 g for 20 minutes, and 10,000 g for 30 minutes). The conditioned medium were incubated with phosphatidylserine binding protein-coated magnetic particles (MPs) for 2 hours at 4° C. with rotator. The MPs were washed with washing buffer and incubated with anti-Her2 fusion proteins for 30 minutes at room temperature with rotator. Unbound anti-Her2 fusion proteins were washed out with washing buffer and MPs were subjected to bioluminescence measurement to determining the presence of Her2-positive exosomes. After bioluminescence detection, the MPs were incubated with elution buffer for 20 minutes at room temperature. Western blot was used to determine the CD9 expression level of eluted exosomes as an internal control.

```
DNA sequence of anti-Her2 fusion protein (SEQ ID NO: 1):
GACCTGGGTAAAAAACTGCTGGAAGCGGCTCGTGCTGGTCAAGATGAT

GAAGTGCGTATCCTGATGGCTAATGGTGCTGATGTGAACGCGAAAGATTTTTATG

GCATTACCCCGCTGCATCTGGCAGCAGCATACGGTCACCTGGAAATCGTGGAAGT

TCTGCTGAAACATGGCGCGGATGTGAACGCCCACGACTGGAATGGTTGGACGCC

GCTGCATCTGGCTGCGAAATATGGCCACCTGGAAATTGTCGAAGTGCTGCTGAAA

CATGGCGCAGATGTTAACGCTATCGACAATGCGGGTAAAACCCCGCTGCACCTG

GCAGCAGCTCATGGTCACCTGGAAATTGTTGAAGTCCTGCTGAAATACGGCGCCG

ATGTCAACGCACAGGACAAATTTGGTAAAACGGCTTTCGATATTAGCATCGACA

ACGGCAATGAAGATCTGGCCGAAATCCTGCAAAAACTGGGTGGCGGTGGCAGCC

GTAGCGACCTGGGTAAAAAACTGCTGGAAGCTGCTCGTGCGGGTCAAGATGATG

AAGTGCGTATTCTGATGGCTAACGGTGCCGATGTCAATGCGAAAGATGAATATG

GCCTGACCCCGCTGTACCTGGCAACGGCTCATGGTCACCTGGAAATTGTGGAAGT

TCTGCTGAAAAACGGCGCAGATGTCAATGCGGTGGACGCCATCGGTTTTACCCCG

CTGCATCTGGCGGCCTTCATTGGCCACCTGGAAATCGCGGAAGTTCTGCTGAAAC

ATGGCGCAGATGTCAACGCTCAGGACAAATTTGGTAAAACGGCGTTCGATATTA

GCATCGGCAACGGTAATGAAGACCTGGCCGAAATTCTGCAAAAACTGGGTGGCG

GTTCTGGTGGCGGTAGCGGCGGTGGCAGTATGAAACCGACCGAAAATAATGAAG

ACTTTAACATCGTGGCAGTGGCGAGTAACTTTGCTACGACCGACCTGGACGCTGA

CCGTGGTAAACTGCCGGGCAAAAAACTGCCGCTGGAAGTTCTGAAAGAAATTGA
```

-continued
AGCAAACGCACGTAAAGCAGGTTGCACCCGTGGTTGCCTGATCTGTCTGAGCCAT

ATCAAATGCACGCCGAAAATGAAAAAATGGCTCCCGGGCCGTTGTCACACCTAT

GAAGGTGATAAAGAATCTGCACAGGGCGGTATTGGCGAAGCTATTGTCGATATC

CCGGAAATTCCGGGTTTTAAAGACCTGGAACCGATAGAACAGTTCATCGCGCAA

GTGGATCTGTGCGTTGACTGTACCACGGGCTGCCTGAAAGGTCTGGCCAATGTGC

AGTGTAGTGACCTGCTGAAAAAATGGCTGCCGCAACGCTGTGCTACGTTCGCAA

GCAAAATTCAGGGTCAAGTGGACAAAATCAAAGGTGCAGGTGGTGATAGCCTGA

GCACCCCGCCGACCCCGAGCCCGAGCACCCCGCCGGGCGGTTGCGGTGGCTGTG

GTGGTTGCGGCGGCTGTAGCCTGGAAGGTACCATGAGCGGCCTGAACGATATTTT

TGAAGCGCAGAAAATTGAATGGCATGAA

Protein sequence of anti-Her2 fusion protein (SEQ ID NO: 2)
DLGKKLLEAARAGQDDEVRILMANGADVNAKDFYGITPLHLAAAYGHLEI

VEVLLKHGADVNAHDWNGWTPLHLAAKYGHLEIVEVLLKHGADVNAIDNAGKTPL

HLAAAHGHLEIVEVLLKYGADVNAQDKFGKTAFDISIDNGNEDLAEILQKLGGGGSR

SDLGKKLEAARAGQDDEVRILMANGADVNAKDEYGLTPLYLATAHGHLEIVEVLLK

NGADVNAVDAIGFTPLHLAAFIGHLEIAEVLLKHGADVNAQDKFGKTAFDISIGNGN

EDLAEILQKLGGGSGGGSGGGSMKPTENNEDFNIVAVASNFATTDLDADRGKLPGK

KLPLEVLKEIEANARKAGCTRGCLICLSHIKCTPKMKKWLPGRCHTYEGDKESAQGG

IGEAIVDIPEIPGFKDLEPIEQFIAQVDLCVDCTTGCLKGLANVQCSDLLKKWLPQRCA

TFASKIQGQVDKIKGAGGDSLSTPPTPSPSTPPGGCGGCGGCGGCSLEGTMSGLNDIF

EAQKIEWHE

Figure 2:
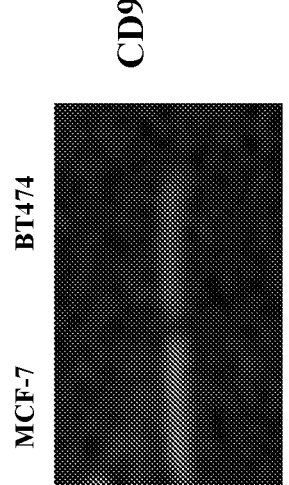
FIG. 2 is a graph showing the amount of Her-2 positive exosomes in cultures of MCF-7 and BT474 cells. Y axis: Relative Light Unit (RLU) ratio; X axis: cell type.
Figure 2:
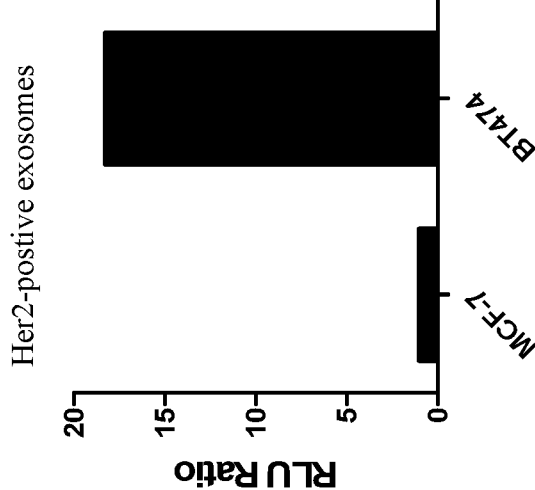

As shown in FIG. 2, the anti-Her fusion protein was capable of positively detecting the presence of HER-2 positive exosomes in MCF-7 and BT474 cells. The amount of bulk extracellular vesicles were quantified using Western blot to detect CD9 expression as an internal control (CD9 is a universal extracellular vesicle marker).

DISCUSSION

Although tumor-derived extracellular vesicles (EVs) are shed or released from tumor cells, their biophysical and biological properties are distinguished from tumor cells. Therefore, strategies used to develop sensors to capture and detect EVs cannot be predictably derived from ones aimed at capturing and detecting tumor cells. First, the size of EVs (nanoscale) are significantly smaller than tumor cells (microscale); thus, the specific makers on the surface of EVs for capture and detection are extremely low as compared to tumor cells. In addition, EVs are derived only partially from the plasma membrane of the tumor cells. Therefore, the specific markers used for capturing and detecting tumor cells may not work to capture and detect of EVs. Cell are living entities. Expression of specific markers on the cell surface is dynamic. Once detection sensors bind to the surface of receptors (markers) of tumor cells, the sensors can be translocated inside the cells by endocytosis. Meanwhile, cells synthesize new receptors that are relocated on the cell surface. The detection sensors can continuously bind to newly synthesized receptors and get incorporated into the cells. As a result, the sensors will accumulated inside of the cells. However, EVs are only membrane-bound vesicles that do not possess endocytosis functionality. Thus, the sensors binding to EVs may overlap with sensors that bind whole tumor cells.

Another difference between detecting and capturing tumor cells and EVs involves steric hindrance and three dimensional structure of the cells and the EVs, and how they bind to their corresponding ligands in the detection sensors. Steric hindrance has a strong influence on the interaction between detection sensors and target receptors. Most surface receptors are partnered with themselves or other receptors to form, for example, homodimer or heterodimer structures. These partnered proteins might block the binding between sensors and target receptors. The partnered proteins will be exposed in a different architecture on the surface of EVs and tumor cells. Thus, the binding interaction will be different because (1) there are far less number of receptors in the EVs, and (2) the binding affinity will be different given the different three-dimensional orientation of the receptors in the EVs and the tumor cells. Accordingly, technology for detecting and capturing tumor cells cannot be predictably applied to EVs. The disclosure provides sensors to detect tumor-derived EVs based on antibody mimetics that have high binding affinity against target receptors on the EVs, optionally with optimized linkers having length and flexibility between the antibody mimetic and bioluminescence protein to avoid steric hindrance between sensors and their target receptors on the EVs.

The data provided herein demonstrates that a fusion protein comprising an antibody mimetic, a bioluminescence protein and a detectable label is able to detect the presence of tumor-derived extracellular vesicles in a sample.

What is claimed is:

1. A method for detecting the presence of circulating extracellular vesicles in a subject, the method comprising
   (a) contacting a biological sample from the subject with a fusion protein comprising the amino acid sequence set forth in SEQ ID NO: 2, and wherein the fusion protein is coupled to a detectable label;
   (b) detecting presence of extracellular vesicles in the sample by detecting the presence of the detectable label coupled to the fusion protein bound to the vesicles.

2. The method of claim 1, wherein the extracellular vesicles are tumor-derived extracellular vesicles.

3. The method of claim 1, wherein the extracellular vesicles are exosomes or microvesicles or a combination thereof.

4. The method of claim 2, wherein the tumor-derived extracellular vesicles are ovarian tumor-derived extracellular vesicles.

5. The method of claim 1, wherein the biological sample is serum or plasma.

6. The method of claim 1, wherein the detectable label comprises a bioluminescent protein.

7. The method of claim 1, further comprising
   (c) isolating the detected extracellular vesicles from the biological sample.

8. The method of claim 1, wherein the fusion protein detectable label conjugate is biotinylated.

9. The method of claim 8, wherein the isolating step comprises contacting the detected extracellular vesicles with streptavidin magnetic beads.

10. The method of claim 1, wherein the method comprises, prior to step (a), isolating extracellular vesicles from serum or plasma from the subject to prepare the biological sample.

11. The method of claim 10, wherein isolating the extracellular vesicles from serum or plasma comprises applying magnetic particles coated with phosphatidylserine binding proteins to the serum or plasma and removing extracellular vesicle-bound magnetic particles from the serum or plasma.

12. A method of detecting the presence of circulating ovarian tumor-derived extracellular vesicles in a subject, the method comprising
   (a) contacting a biological sample from the subject with a fusion protein comprising the amino acid sequence set forth in SEQ ID NO: 2, and wherein the fusion protein is coupled to a detectable label;
   (b) detecting presence of ovarian tumor extracellular vesicles in the sample by detecting the presence of the detectable label coupled to the fusion protein bound to the ovarian tumor extracellular vesicles.

* * * * *